Oct. 1, 1935. J. M. ATER Plant Pat. 142
SPORT OF CITRUS FRUIT
Filed Sept. 2, 1931
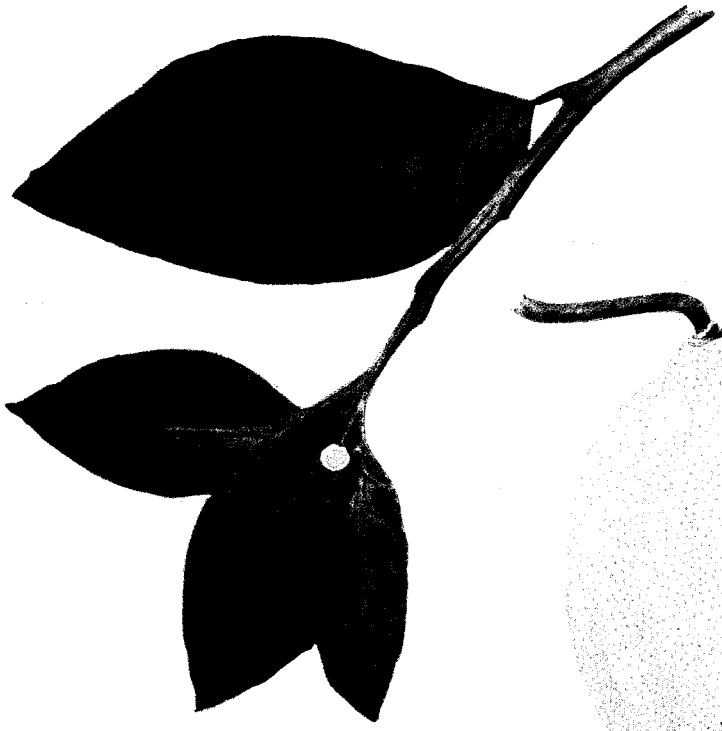
Fig. 1.
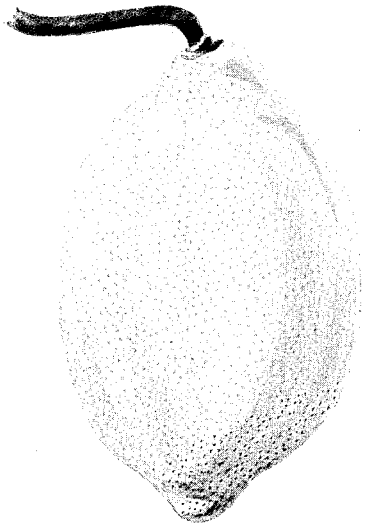
Fig. 2.
Fig. 3.
Inventor
James M. Ater
By A. B. Bowman
Attorney Patented Oct. 1, 1935

Plant Pat. 142

UNITED STATES PATENT OFFICE

142

SPORT OF CITRUS FRUIT

James M. Ater, Chula Vista, Calif.

Application September 2, 1931, Serial No. 560,872

1 Claim. (Cl. 47—62)

My invention relates to a sport of the citrus fruit variety and particularly to the fruit of this variety which possesses characteristics of the fruit of both the orange and lemon trees, and the objects of my invention are:

First, to provide a fruit of the citrus variety the juice of which combines the desired qualities of the orange and the lemon; and Second, to provide a novel juice producing fruit of the citrus variety.

With these and other objects in view as will appear hereinafter, my invention consists of a certain novel fruit of the citrus variety as hereinafter described in detail and particularly set forth in the appended claim, reference being had to the accompanying drawing, in which:

Figure 1 is a perspective view in color of a branch of a tree that produces the fruit and illustrating the foliage thereon; Fig. 2 is a side elevational view in color of the fruit when ripe, and Fig. 3 is a cross section of the fruit in color when ripe.

The principal distinguishing characteristics of my new fruit of the citrus variety are particularly apparent in that it is borne on an orange tree and its interior color is yellow verging on orange, and its exterior color is deep orange, and its exterior shape like a lemon, oblong with umbonate apexes, and the juice is tart resembling the juice of both the orange and lemon in flavor.

*Technical description*

Fruit the size and shape of a large Lisbon lemon. Average from 2¼ to 2½ inches in diameter, from 3½ to 4 inches long. Surface slightly undulating with numerous oil sacs and the color of a navel orange. Rind of medium thickness, peeling more easily than a lemon but not as readily as an orange. Pulp is firm and of medium texture. Segments from 8 to 10 in number. Seeds scarce and small, seldom more than 5 or 6. Fruit produces quantities of juice which is less sweet than orange juice and less acid than lemon juice. It is a perfect combination of the flavors of both orange and lemon and makes a delicious drink. Trees of this variety, using sour orange as a root stock, are of medium size and vigorous growth with thornless limbs and dark green leathery leaves which are more slender and pointed than lemon or orange leaves. Flowers are pure white like the orange but smaller and not as sweetly scented. The budded trees show all characteristics of the sport.

The quality of the flesh of the fruit is more that of the lemon than of the orange being rather highly acid but with a flavor distinguished from that of either the lemon or orange or any other known citrus fruit. The oil cells are flush with the surface. The odor of the fruit is more like the orange than the lemon. The fruit stands shipping better than the lemon. The fruit has a medium amount of rag which is medium in texture. The bulk of the crop is from February to May but the fruit may be picked any time of the year. The tree stands climate, insects and diseases similarly to the lemon tree. The fruit is distributed throughout the inside and outside of the tree, the outer fruit being exposed.

Having thus described my invention, what I claim as new and desire to secure by Letters Patent is:

The citrus variety herein disclosed, characterized by fruit which when ripe has exterior color deep orange, interior color yellow verging on orange, exterior shape like a lemon oblong with umbonate apexes, and juice that is tart resembling the juice of both the orange and lemon in flavor.

JAMES M. ATER.